(12) United States Patent
Gaston et al.

(10) Patent No.: US 6,723,703 B2
(45) Date of Patent: Apr. 20, 2004

(54) THERAPEUTIC USE OF AEROSOLIZED S-NITROSOGLUTATHIONE IN CYSTIC FIBROSIS

(75) Inventors: Benjamin Gaston, Charlottesville, VA (US); Jonathan S. Stamler, Chapel Hill, NC (US)

(73) Assignees: Duke University, Durham, NC (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 10/380,763
(22) PCT Filed: Oct. 15, 2001
(86) PCT No.: PCT/US01/27768
§ 371 (c)(1), (2), (4) Date: Mar. 24, 2003
(87) PCT Pub. No.: WO02/32418
PCT Pub. Date: Apr. 25, 2002

(65) Prior Publication Data
US 2003/0212004 A1 Nov. 13, 2003

Related U.S. Application Data
(60) Provisional application No. 60/240,708, filed on Oct. 16, 2000.

(51) Int. Cl.$^7$ .......................... A61K 38/00; A61K 31/13
(52) U.S. Cl. ........................................ 514/18; 514/645
(58) Field of Search .................. 514/18, 645

(56) References Cited

U.S. PATENT DOCUMENTS

| 4,900,719 A | * | 2/1990 | Means et al. ............... 514/18 |
| 5,859,058 A | * | 1/1999 | Zimmerman et al. ....... 514/565 |
| 6,314,956 B1 | * | 11/2001 | Stamler et al. ........ 128/200.24 |
| 6,331,543 B1 | * | 12/2001 | Garvey et al. ............ 514/250 |
| 6,359,182 B1 | | 3/2002 | Stamler et al. ............ 568/949 |
| 2001/0012834 A1 | | 8/2001 | Stamler ..................... 514/18 |
| 2002/0002136 A1 | * | 1/2002 | Hebert ....................... 514/18 |

FOREIGN PATENT DOCUMENTS

WO    WO 98/52580    11/1998

OTHER PUBLICATIONS

Snyder, A.H., et al, Am J Respir Crit Care Med 165, 1–5, (2002).

* cited by examiner

*Primary Examiner*—Raymond J. Henle, III

(57) ABSTRACT

The present invention is directed to the treatment of cystic fibrosis that involves the administration of a nitrosylating agent, such as S-nitrosoglutathione or ethyl nitrite.

7 Claims, 5 Drawing Sheets

THERAPEUTIC USE OF AEROSOLIZED S-NITROSOGLUTATHIONE IN CYSTIC FIBROSIS

CROSS-REFERENCE TO RELATED APPLICATIONS

The application is a filing under 35 U.S.C. 371 of PCT/US01/27768, filed Oct. 15, 2001, which claims the benefit of U.S. Provisional Application No. 60/240,708, filed Oct. 16, 2000, which is incorporated herein by reference. PCT/US01/27768 was published in English as WO 02/32418 A1 on Apr. 25, 2002.

BACKGROUND

Cystic fibrosis (CF) is an autosome recessive disease. Affected patients have an average life expectancy of 30 years. This early mortality is primarily related to lung disease, in particular for 95% of patients, death results from progressive respiratory failure associated with impaired mucus clearance and excessive overgrowth of bacteria and fungi in the airways. The lung disease is characterized by 1) abnormal salt and water transport in the airway epithelium, such that too much sodium and too little chloride crosses the epithelial membrane; 2) a defect in glutathione transport out of airway epithelial cells; 3) inspissated secretions and oxidant damage, in part related to salt, water, and glutathione transport abnormalities; 4) impaired ciliary motility associated with thick secretions; 5) chronic colonization with denitrifing organisms such as *Pseudomonas aeruginiosa* and *Aspergillus fumigatus*; and 6) chronic bronchoconstriction associated with recruitment of neutrophils and other inflammatory cels and associated release of bronchoconstricting mediators and, as a result of all of these factors, chronic, progressively worsening, dyspnea.

Cystic fibrosis is caused by mutations in a membrane-associated chloride channel, the cystic fibrosis transmembrane regulatory protein (CFTR). The most common mutation, accounting for 70% of alleles, is a 3 base pair (single amino acid) deletion at the 508 position on the first ATP binding domain, the (ΔF508) mutation. This is referred to as a class II mutation in that intact and potentially functional protein is degraded in the endoplasm reticulum because of a small folding error. It is known that his degradation can be bypassed in vitro by hypothermia and by treatment with compounds,such as glycerol and phenylbutyrate. These treatments result in functional expression of (ΔF508) CFTR on the cell surface. It has recently been proposed that CFTR degradation in the endoplasmic reticulum (ER) is mediated by the ubiquitin-proteasome system. We have preliminary evidence that S-nitrosoglutathione (GSNO) inhibits the ubiquitin proteosome pathway, stabilizing the expression of post-translationally/degradation-regulated proteins such as hypoxy inducible factor 1-$\mu$.

Furthermore, GSNO is of interest in cystic fibrosis for several established reasons. We have shown in 1993, that it is a compound present endogenously in the airways and has activity as a bronchodilator. GSNO is also known to increase ciliary beat frequency, augmenting airway clearance to inhibit amiloride-sensitive sodium transport, augmenting airway lining fluid salt and water retention. It has established antimicrobial properties, inhibiting the replication of viruses, bacteria, and parasites. We have recently discovered that levels of GSNO are low in the bronchoalveolar lavage fluid of patients with mild cystic fibrosis. All of these established functions could have a salutary effect in CF.

Surprisingly, we have discovered that the treatment of cells homozygous to the (ΔF508) mutation with 100 $\mu$M GSNO increases the expression of CFTR and increases the maturation of CFTR (see FIG. 1). We have also discovered that inhalation of GSNO at concentrations effective to enhance the production of CFTR (a dose of about 0.05 ml/kg of a 10 mM GSNO solution) results in improved oxygenation. Finally we have shown that GSNO is well tolerated in CF and has no adverse systemic affects. Therefore, since replacement of low levels of GSNO is well tolerated, acutely beneficial, and can increase the amount of functional CFTR expressed on the cell surface, its use is proposed to benefit people with the disease.

BRIEF SUMMARY OF INVENTION

The present invention is directed to composition and method for treating CF patients. The method comprises the delivery of S-nitrosoglutathione (GSNO) in concentrations equal to or in excess of 500 nmole/kg (175 mcg/kg), or other nitrosylating agents such as ethyl nitrite, to epithelial surfaces of patients with cystic fibrosis for the purpose of insuring adequate concentrations of S-nitrosylating agent on the epithelial surfaces of CFTR and epithelial function. The compositions of the present invention comprise a nitrosonium donor including, but not limited to GSNO and other S-nitrosothiols (SNOs) in a pharmaceutically acceptable carrier that allows for administration by nebulized or other aerosol treatment to patients with cystic fibrosis.

Increased expression of the immature non-glycosylated protein (140 kDa) reflects decreased degradation of the immature protein in the endoplasma retimulum The appearance of a band at 180 kDa (mature protein) reflects maturation of the protein in the endoplasmic reticulum, an expression of a form capable of being expressed on the cell surface representative of three experiments. The full maturing of the protein accommodates for the ΔF508 mutation.

Figure 1:
FIG. 1. S-Nitrosoglutathione stabilizes and allows maturation of human CFTR protein bearing the ΔF508 mutation. Human pancreatic adenocarcinoma cells from a patient homozygous for ΔF508 (CFPAC-1) were grown to confluence and treated with medium alone (control) or 500 nM, 1 $\mu$M, 5 $\mu$M, 10 $\mu$M or 100 mM GSNO for 6 hours. The cells were harvested, lysed, resuspended in NP40 buffer and underwent Western Blot analysis with anti-CFTR antibody. Results are shown in FIG. 1 where Lane A shows expression of the immature non-glycosylated protein (140 kDa), Lane B shows expression of partially matured protein (about 160 kDa), and Lane C shows expression of mature protein (180 kDa).
Figure 2:
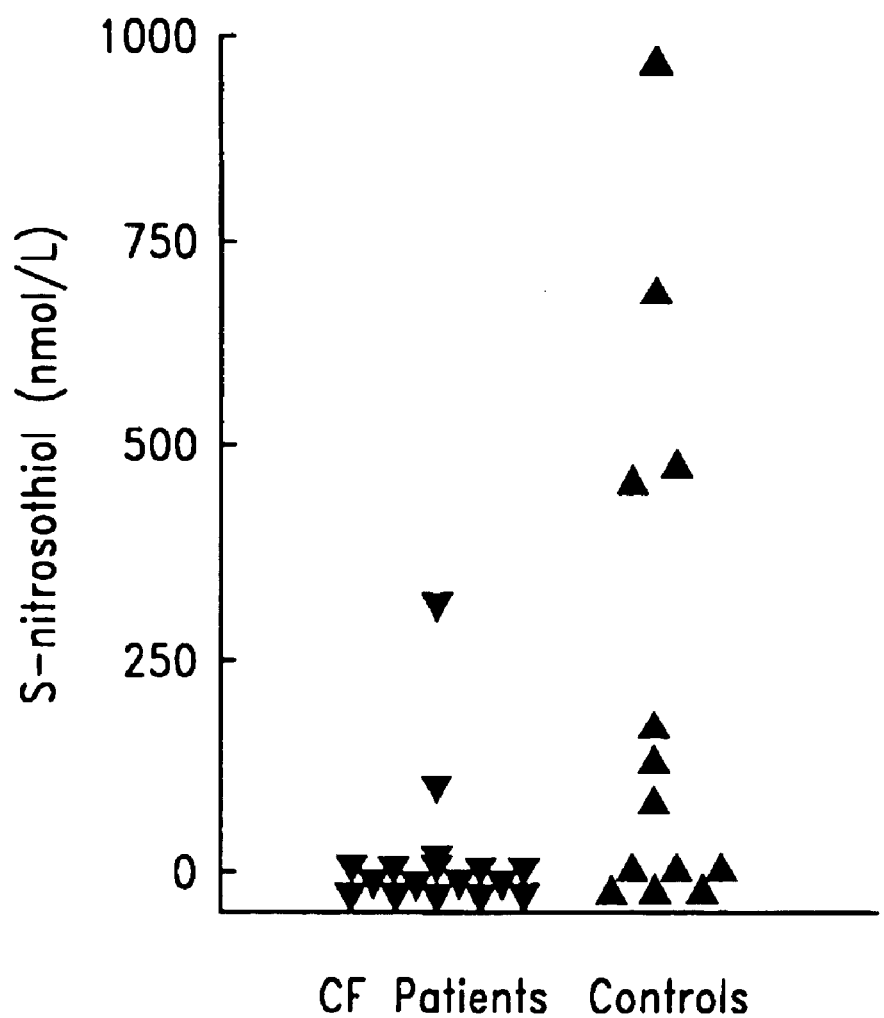

FIG. 2. S-Nitrosothiol levels are low in the cystic fibrosis airway. Subjects with mild cystic fibrosis and control subjects underwent bronchoalveolar lavage. Lavage fluid was frozen (−80° C.) and subsequently underwent blinded analysis for S-nitrosothiol content using an established method of reduction (1 mM cysteine, 100 $\mu$M CuCl; 50° C., pH 6.5) to nitric oxide followed by chemiluminescent analysis. S-Nitrosothiols were only measurable in two CF patients, and Rank Sum analysis showed that values were lower than in controls (p<0.01).

Figure 3:
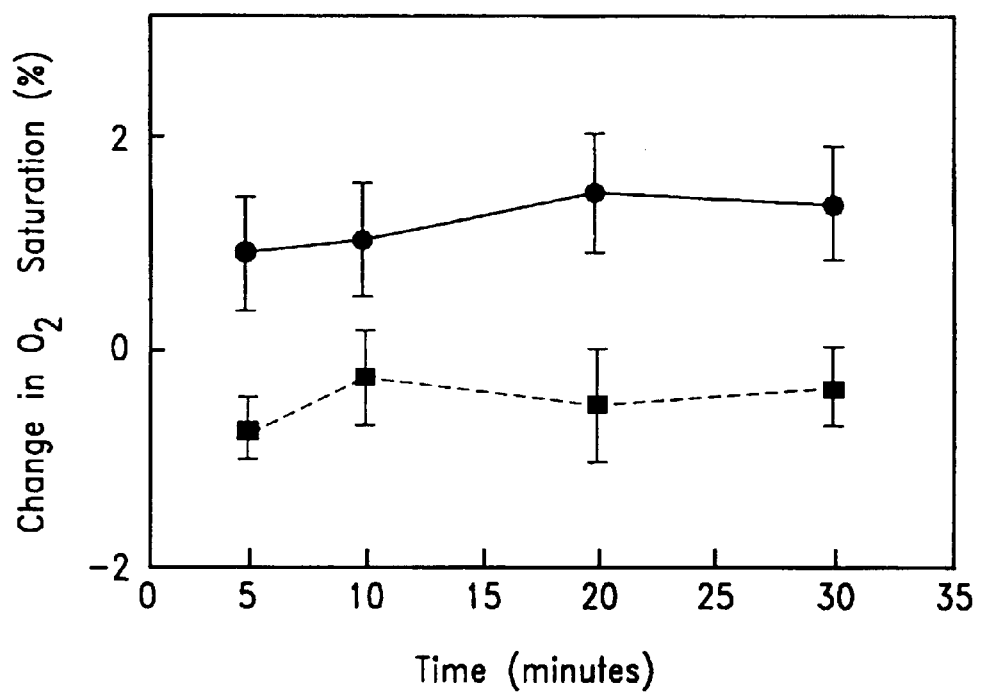

FIG. 3. Inhalation of 0.05 ml/kg of 10 mM GSNO results in improved oxygenation in patients with CF. In a double-blind, placebo-controlled study, patients with CF received GSNO in 10 mM phosphate buffered saline (PBS) (n=9) or 10 mM PBS alone (n=11) by nebulizer. The two groups were matched with respect to age, vital signs, oxygen saturation, vital capacity, $FEV_1$, and $FEF_{25-75}$ (p=7). Change in oxygen saturation from pretreatment baseline is recorded as a function of time. Results are shown in FIG. 3 where the continuous line represents the GSNO group and the line composed of dashes represents the PBS alone group. As shown in FIG. 3, subjects in the GSNO group had a greater improvement in oxygen saturation than those in the PBS group that was sustained throughout the study (p<0.001 by ANOVA).

Figure 4:
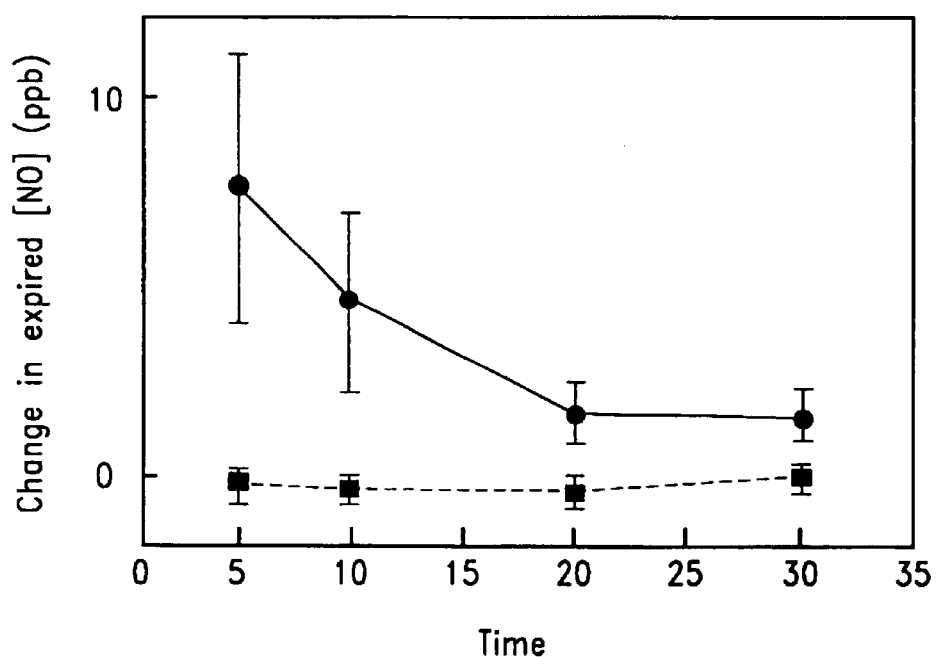
Figure 5A:
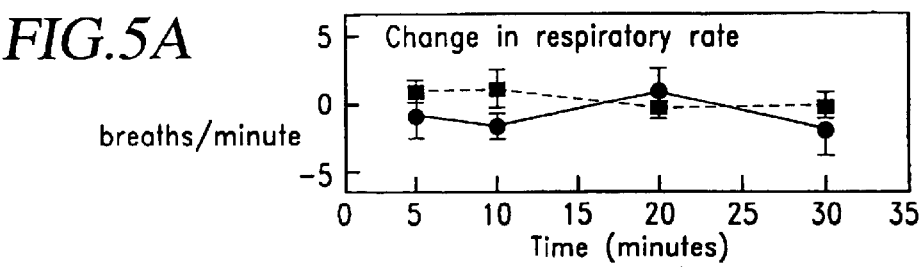
Figure 5B:
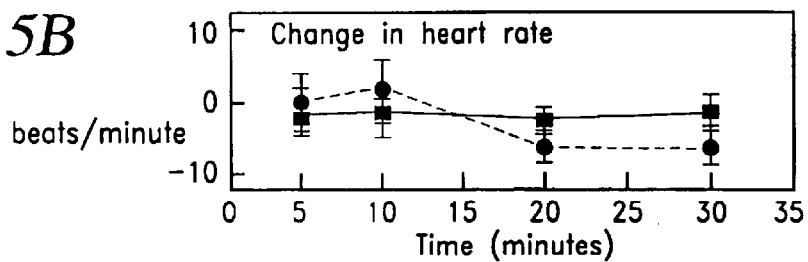
Figure 5C:
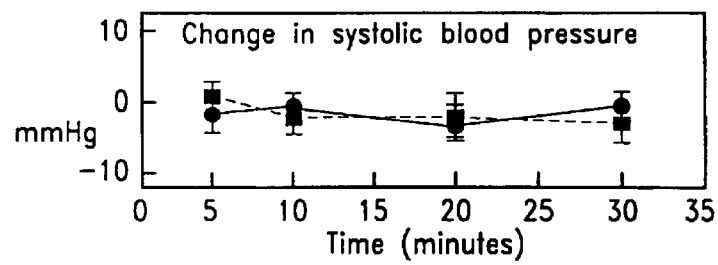
Figure 5D:
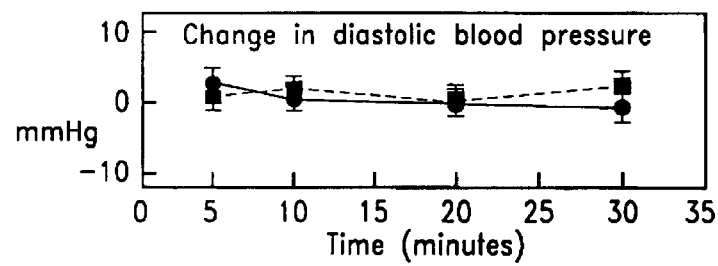
Figure 5E:
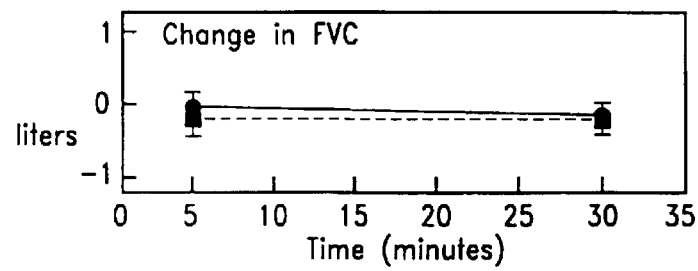
Figure 5F:
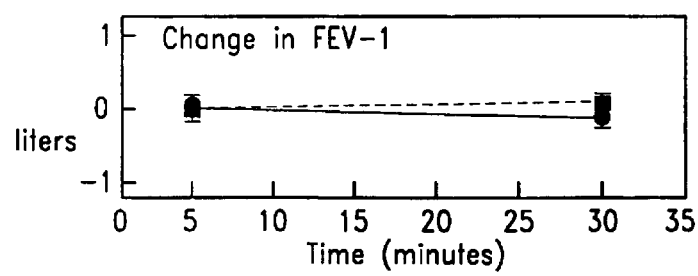

FIG. 4. Inhaled S-nitrosoglutathione cases increased expired nitric oxide (NO) concentration in CF. Data presented represent the two groups described in FIG. 3, but with respect to expired nitric oxide concentration (measured off-line with chemiluminescence in accordance with American Thoracic Society guidelines). Results are shown in FIG. 4 where the continuous line represents the GSNO group and the line composed of dashes represents the PBS alone group. As shown in FIG. 4, change in expired NO from baseline is higher in the GSNO group at all time points (p<0.001 by ANOVA). Note that the change at 30 minutes is less pronounced than at 5 minutes, though improvement in oxygenation is as dramatic at 30 minutes as at 5 minutes. This finding, coupled with the relatively low levels of expired NO after GSNO treatment, suggests that the effect of GSNO on improved oxygenation does not require its breakdown to form the nitric oxide radical but may, instead, involve transuitrosation reactions with airway proteins. These S-nitrosylation reactions may be critically important to smooth muscle relaxation, antimicrobial effects and modification of ion channel function.

FIGS. 5A, 5B, 5C, 5D, 5E and 5F. Inhaled S-nitrosoglutathione is well tolerated in CF patients. As shown in FIGS. 5A, 5B, 5C, 5D, 5E, and 5F, where the continuous lines represent the GSNO group and the fines composed of dashes represent the PBS alone group, no acute change in vital signs or lung function was observed in patients receiving GSNO using the study protocol described in conjunction with FIG. 3 that increased oxygen-saturation and increased expired NO.

DETAILED DESCRIPTION OF THE INVENTION

As used herein, the term "treating" includes alleviating the symptoms associated with a specific disorder or condition and/or preventing or eliminating said symptoms. In particular, treating CF includes causing one or more of the following: enhanced CFTR activity, augmented airway hydration, improved mucociliary clearance, bronchodilatation, and antimicrobial effect.

As used herein, an "effective amount" means an amount sufficient to produce a selected effect. For example, an effective amount of GSNO is an amount sufficient to alleviate the symptoms associated with CF.

The present invention is directed to use of a composition comprising a S-nitrosothiol in a form suitable for administration to a CF patient and formulated to maximize contact with epithelial surfaces of the respiratory tract. S-Nitrosoglutathione is the most abundant of several endogenous S-nitrosothiols. It is uniquely stable compared, for example, to S-nitrosocysteine unless specific GSNO catabolic enzymes are upregulated. Such enzymes can include γ-glutamyl-transpeptidase, glutathione-dependent formaldehyde dehydrogenase, and thioredoxi-thioredoxin reductase. Additionally, there is evidence that prokaryotic enzymes may exist which may limit the bactericidal effect of GSNO. For this reason, coadministration of inhibitors of GSNO prokaryotic or eukaryotic GSNO catabolism may at times be necessary. This kind of inhibitor would include, but not be limited to, acivicin given as 0.05 ml/kg of a 1 mM solution to achieve an airway concentration of 1 $\mu$M.

In part, the administration of a S-nitrosothiol reverse the ion channel abnormality associated with CF and alleviates the bronchoconstriction characteristic of CF. The present methodology provides a new route of antimicrobial therapy for CF, of particular relevance because many patients have organisms that are resistant to all available conventional antimicrobial agents. The present invention also delivers nitrogen oxide to the CF airway, and surprisingly, increases the expression and maturation of CFTR.

Additional NO donors and transnitrosating agents suitable for use in the present invention in place of GSNO include compounds of the general formula X—NO, where X=RS, and R is selected from the group consisting of cysteine, homocysteine, N-acetyl cysteine, cysteinyl glycine, albumin, and other proteins; alternatively, X is selected from the group consisting of ethyl propyl tertbutyl methyl, and other alkyl hydrocarbons. Also included as an active compound is nitroglycerine, because both the nitro moieties (as nitrosating species) and the glycerin (metabolized to glycerol) can increase the expression of CFTR.

In one embodiment, the invention consists of the delivery of S-nitrosoglutathione in concentrations equal to or in excess of 500 nmole/kg (175 mcg/kg), or other nitrosylating agents such as ethyl nitrate or ethyl nitrite, to epithelial surfaces of patients with cystic fibrosis. The method provides adequate concentrations of S-nitrosylating agent on the epitheilal surfaces of CFTR and epithelial function to alleviate CF symptoms. These nebulized treatments, including GSNO, other SNO's, and/or other NO$^+$ donors with or without an inhibitor of breakdown can be given on a periodic basis such as every 4, 6, or 8 hours to prevent accumulation of mucus, bronchoconstriction and bacterial growth in the CF airway, or given acutely during an exacerbation of bronchoconstriction, mucus plugging, and bacterial bronchitis/bronchiolitis to patients with cystic fibrosis. Accordingly, the S-nitrosylating agents of the present invention can be administered in an aerosolized form as preventive therapy for cystic fibrosis lung disease, or as acute therapy for cystic fibrosis lung disease or to provide relief from chronic obstructive pulmonary disease and bronchiectasis.

In accordance with one embodiment aerosolized S-nitrosoglutathione and/or other S-nitrosothiols are administered in a concentration of 10 mM using a dose of 0.05 ml/kg according to the following calculation:

a. S-Nitrosoglutathione levels in the airways of normal subjects are generally between 200 nM and 2 $\mu$M (in specimens undiluted by bronchoalveolar lavage).

b. Airway S-nitrosoglutathione levels in patients with pneumonia may be in excess of 10 $\mu$M.

c. Airway lining fluid/extra cellular lung water volume is on the order of 10 ml/kg in normal subjects.

d. Maximal direct delivery to the lower airway using conventional nebulizer systems is 20% of the administered dose.

e. S-Nitrosoglutathione has a IC$_{50}$ in relaxing human airway smooth muscle preparations of approximately 10 $\mu$M.

f. Therefore, providing ($5\times10^{-5}$ l/kg$\times 1\times10^{-2}$ M GSNO in $1\times10^{-2}$ l/kg volume)$\times 0.2=10\times10^{-6}$ M concentration in the airway, in the physiologically relevant and pharmacologically active range.

In one preferred embodiment an aerosol of 10 mM GSNO, at a dose of 0.05 ml/kg, is delivered to the CF airway on a daily basis. Additional embodiments include 1) the use of a similar concentration by dry powdered inhaler, and 2) delivery of greater concentrations to the lower respiratory tract by an aerosol bronchoscopy, 3) endoscopic retrograde cholangiopancreatographic delivery, 4) delivery of an aerosol preparation through the gastrointestinal mucosa, 5) by atomizer to the nasal mucosa and osteomeatal complex, 6) to the eustachian tube, to the vas deferens, cervix, or oviduct. This dosing has as its objective restoring normal levels of GSNO to the airway. In this regard, we have shown that the majority of patients (15 our of 17) with mild cystic fibrosis undergoing bronchoalveolar lavage have undetectable SNO levels in their airways whereas the majority of controls have detectable levels (as high as 1 $\mu$M, despite significant dilution effects involved in the technique) (FIG. 2.)

A broad range of symptoms associated with CF can treated by use of an inhaled nitrosylating agent. For example, the use of inhaled GSNO in doses of about 0.15 to about 0.03, more preferably about 0.05 ml/kg of a 10 mM concentration can be used to treat bronchoconstriction (airway smooth muscle tightening), and to treat hypoxia in cystic fibrosis. In addition, inhaled S-nitrosoglutathione can be used to prevent the long term deterioration of lung function, dyspnea, cough, chronic airway infection, bronchiectasis, atelectasis, pneumothorax, and respiratory failure in patients with cystic fibrosis. These conditions arise because of a defect in maturation and expression of functional CFTR in the airway epithelium The ideal dose is 0.05 ml/kg of 10 mM GSNO delivered by nebulization. Alternative doses may be applied in certain circumstances.

In accordance with one embodiment, the S-nitrosothiol compositions used in the present invention are formulated in an oral dosage form Of note, GSNO is stable at acid pH. Most patients with cystic fibrosis have decreased pancreatic bicarbonate secretion and GSNO is anticipated to be bioavailable in the digestive system past the level of the duodenum. The ideal dose is on the order of 150 mcg/kg. This can be given up to 6 times a day. However, different doses and frequencies may at times be required and/or also claimed. The method comprises administering GSNO in an oral dosage form for increasing gastrointestinal epithelial function in cystic fibrosis patients with meconium ileus, meconium ileus equivalent, and/or refractory malabsorption. In another embodiment, surgical installation of S-nitrosothiols, such as S-nitrosoglutathione, in patients with cystic fibrosis can be conducted using dysfunctional tubular epithelial structures, including endoscopic injection in the drainage system of the paranatal sinuses, in the sinuses themselves, in the eustachian tubes, in the hepatobiliary collecting system, in the pancreatic duct, in the uterine cervix, in the fallopian tubes. In addition, surgical installation into the vas deferens for the purpose of increasing the function of epithelium rendered incapable of hydrating secretions and clearing viscus secretions by virtue of mutations associated with loss of function of the CFTR protein is also encompassed in the present invention. For example, aqueous S-nitrosothiol preparations can be used in surgical processes for cleaning sinuses and sinus osteae and eustachian tubes, for endoscopic retrograde cholangiopancreatography (ERCP) treatment of cholestasia arising from hepatobiliary sludging, and for treatment and prevention of pancreatitis, for endoscopic treatment of inspissates mucus in the uterine cervix or oviduct and for treatment and prevention or infertility in men arising from inspecific mucus in the vas deferens—all these indications are limited to patients having CF characterized by abnormal CFTR expression.

Many variations will be obvious to those skilled in the art. Therefore, the invention is defined by the claims.

What is claimed is:

1. A method for treating cystic fibrosis, said method comprising the step of administering a therapeutically effective amount of a composition comprising S-nitrosoglutathione to a patient having cystic fibrosis, wherein the composition is formulated as a powder or an aerosol and administered to the nasal mucosa and osteomeatal complex.

2. The method according to claim 1 wherein the composition comprises about 100 to about 150 mcg/kg of GSNO and the composition is delivered by dry powdered inhaler, metered dose inhaler, or alternative nebulization systems selected from the group consisting of ultrasonic, supersonic, or breath actuated nebulizer.

3. A method for treating cystic fibrosis comprising the step of administering a composition comprising a nitrosylating agent and an inhibitor of an enzyme that catabolizes S-nitrosothiol to a patient having cystic fibrosis.

4. The method of claim 3 wherein the composition comprises 0.05 ml/kg of 10 mM GSNO in conjunction with bathocouproine disulfinate and/or aurothioglucose.

5. A method of enhancing the expression and maturation of CFTR, said method comprising contacting the respiratory epithelium with a composition comprising a nitrosylating agent.

6. The method according to claim 5 wherein the nitrosylating agent is selected from the group consisting of S-nitrosoglutathione and ethyl nitrite.

7. A method for preventing cough, dyspnea and chronic bacterial infection in cystic fibrosis comprising the step of administering a therapeutically effective amount of a composition comprising S-nitrosoglutathione formulated as a powder or an aerosol to the nasal mucosa and osteomeatal complex of a patient having cystic fibrosis.

* * * * *